United States Patent [19]
Opelt et al.

[11] 4,168,700
[45] Sep. 25, 1979

[54] DETERMINATION OF BLOOD LOSSES DURING ENDOSCOPIC OPERATIONS

[75] Inventors: Bernd Opelt, Neuwied; Helmut Wurster, Oberderdingen, both of Fed. Rep. of Germany

[73] Assignee: Richard Wolf GmbH, Knittlingen, Fed. Rep. of Germany

[21] Appl. No.: 841,368

[22] Filed: Oct. 12, 1977

[30] Foreign Application Priority Data

Oct. 13, 1976 [DE] Fed. Rep. of Germany ....... 2646079

[51] Int. Cl.² ............................................. A61B 5/00
[52] U.S. Cl. ..................................................... 128/630
[58] Field of Search ............. 128/2 L, 2 R, 2 G, 2 B, 128/240, 214 E, 276, DIG. 13; 23/258.5; 210/321

[56] References Cited

U.S. PATENT DOCUMENTS

| | | | |
|---|---|---|---|
| 3,168,218 | 2/1965 | Funk et al. | 128/DIG. 13 |
| 3,604,419 | 9/1971 | Diskin et al. | 128/DIG. 13 |
| 3,636,940 | 1/1972 | Gravlee | 128/241 |
| 3,812,482 | 5/1974 | Clark | 128/DIG. 13 |

FOREIGN PATENT DOCUMENTS 1020536  2/1966  United Kingdom ..................... 128/2 L

*Primary Examiner*—William E. Kamm
*Attorney, Agent, or Firm*—Kinzer, Plyer, Dorn & McEachran

[57] ABSTRACT

This disclosure relates to the determination of blood loss during endoscopic operations, particularly, during transurethral resectomy. It is known in such operations to employ continuous irrigation using sterilized water which is fed into the body cavity through the endoscope and fed out again mixed with the lost blood. According to the disclosure a method is provided wherein the specific blood content is found from one of the characteristics of the outgoing water which alters with the blood content: to determine the blood lost this specific blood content is compared with the rate of flow of the monitored outgoing flushing water.

8 Claims, 1 Drawing Figure

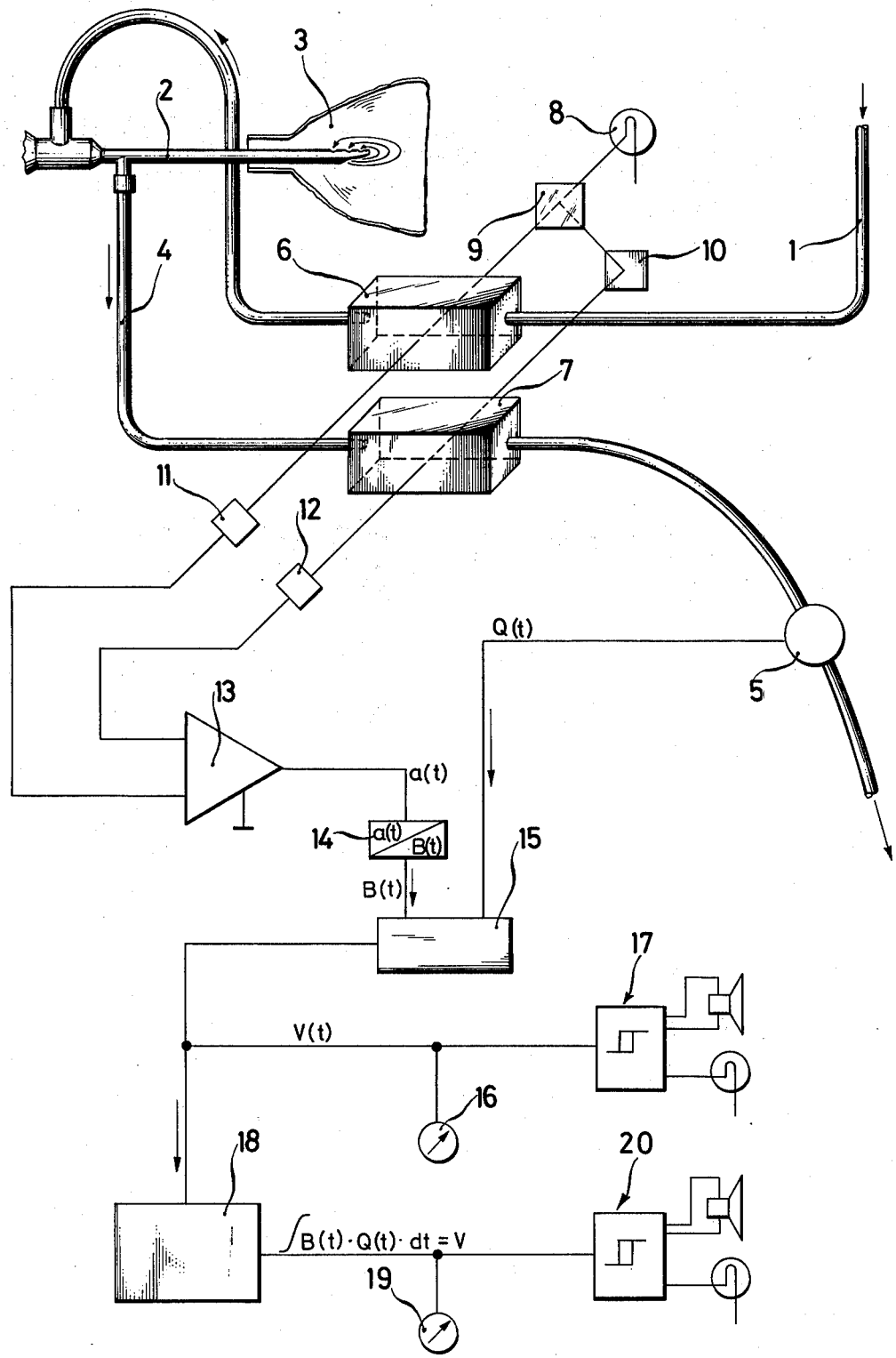

DETERMINATION OF BLOOD LOSSES DURING ENDOSCOPIC OPERATIONS

BACKGROUND OF THE INVENTION

The present invention relates to methods of and apparatus for determining blood losses during endoscopic operations, and especially during urethral resectomy, of the kind in which continuous irrigation is employed, using sterilised water which is fed into the body cavity through the endoscope and is fed out again mixed with the blood which has been lost.

During endoscopic operations, and particularly during transurethral electrical resectomy, losses of blood occur if blood vessels are cut into and it is essential for these to be kept within bounds by deliberately coagulating the blood vessels at the appropriate points. If, during resectomy in the bladder for example, the irrigating water became heavily impregnated with blood and as a result the vision of the operator was obscured, then with conventional instruments the bladder was emptied and filled again with clean sterilised water. From the number of filling operations and the discoloration of the irrigating water in each case, which is dependant on the amount of blood present, it was possible for an experienced operator to estimate the blood losses and if necessary give a blood transfusion.

However, the introduction of resectoscopes designed for continuous irrigation means that it is no longer possible to estimate blood losses on the basis of experience. The fact is that even when there is severe bleeding from large vessels, then because of the continuous flushing vision is never impaired during the resection and the operator has no clue to help him to answer the question of how much blood is being lost at any given time and when it is necessary to coagulate an injured blood vessel. In particular, the fact that the viewing conditions are at all times good may tempt an inexperienced operator to carry on with the resection uninterruptedly, without coagulating larger vessels if this has become necessary in the meantime. This may have serious consequences particularly if so-called sinus bleeding occurs, which may not be realised immediately because of the continuously good viewing conditions.

It is an object of the invention to provide a method of and apparatus for determining blood losses during endoscopic operations which, despite the use of continuous irrigation, at all times give the operator an accurate indication of the instantaneous, and if required the total, blood loss and makes it easier for him to decide, as he could previously only do empirically, whether vessels have to be coagulated or even whether a blood transfusion has to be given.

SUMMARY OF THE INVENTION

To achieve this and other objects, the method hereinbefore referred to is so established in accordance with the invention by determining the specific blood content $B(t)$ from one of the characteristics of the outgoing water which varies with the blood content, and the blood loss $V(t)$ is determined by comparing this blood content with the flow rate $Q(t)$ of the outgoing irrigating water, which is measured. One such characteristic is for example the colour density or optical transmission of the outgoing irrigating water, which depends on the specific blood content $B(t)$ of the irrigating water.

Thus, the colour density (absorbance) for example of the irrigating water fed out may be compared with the colour density of the irrigating water fed in and and the instantaneous blood content $B(t)$ determined from the value $a(t)$ given by the comparison by reference to the absorbance curve for blood in water. If at the same time the amount of outgoing irrigating liquid at any given time $Q(t)$ is measured with a flow meter, the instantaneous blood loss $V(t)$ can be found by multiplying the values $Q(t)$ and $B(t)$.

In apparatus for carrying out the method, an electrical signal corresponding to the instantaneous blood loss $V(t)$ may be fed to the input of a first alarm which gives a signal when a given adjustable threshold value for blood loss is exceeded. In addition, the electrical signal corresponding to the instantaneous blood loss $V(t)$ may be integrated in an integrator. The integrator then feeds a signal representing the total blood loss $V$ to the input of a second alarm which gives an alarm signal when a given adjustable threshold value is exceeded, this alarm signal differing from that from the first alarm. Finally, the values for the instantaneous blood loss $V(t)$ and the total blood loss $V$ may also be displayed visually.

In this way it is possible for the operator at all times to monitor the blood loss as it occurs and to discover whether in fact any blood vessels have been cut into need to be coagulated because of the prevailing blood loss and whether, should the total blood losses eventually become excessive, a blood transfusion is required.

BRIEF DESCRIPTION OF THE DRAWING

In order that the invention may be more clearly understood, reference will now be made to the accompanying drawing which is a diagram of a practical embodiment of apparatus according thereto.

DETAILED DESCRIPTION OF A PREFERRED EMBODIMENT

Referring now to the drawing, sterilised irrigating water passes from an irrigator (not shown) along a pipe 1 to a continuously irrigating resectoscope 2 and into the patient's bladder 3 and from there back through the instrument to an outlet pipe 4. This pipe thus conveys irrigating water which contains blood when there is bleeding from blood vessels, and the instantaneous quantity of this water i.e. its rate of flow $Q(t)$ is determined by a flow meter 5.

As has already been mentioned, the specific blood content in the outgoing irrigating water may be determined from the optical characteristics, which vary with the blood content, by deriving electrical values from the colour density or absorbance of the ingoing irrigating water and comparing them, by forming a difference for example.

For this purpose, in the present embodiment a chamber 6 through which the sterilised irrigating water flows and a chamber 7 through which the outgoing water flows are fitted in pipes 1 and 4 respectively.

The chambers are irradiated from one side with light which, to avoid problems when calibrating the arrangement, usefully is of the same intensity and has the same spectral distribution in the case of both the chambers irradiated. The light travels from a lamp 8 through a splitting mirror 9 where it is divided into two parts, one passing through the chamber 6 and the other through a deflecting prism 10 to the chamber 7.

The two chambers 6 and 7 have associated with them, on the side which in each case is remote from the light source, photoelectric receivers 11, 12 which receive a proportion of the light emerging from the bulbs and generate electrical output signals from it. This being the case, the signal from receiver 11 gives an indication of the colour density of the ingoing irrigating water and the signal from receiver 12 gives an indication of the colour density of the outgoing irrigating water. These two signals are fed to the inputs of a difference amplifier 13 and subtracted. The result which is received is an electrical difference signal a(t).

As yet, this signal a(t) does not give any direct indication of the actual specific blood content since no allowance has yet been made for the absorbance function of the mixed liquid represented by blood in water. The absorbance curve for blood in water is known or can be determined relatively easily to act as a reference curve and is fed into a measured value converter. Such reference curves can in fact be obtained commercially.

The converter 14 thus receives the difference signal a(t) and by means of a calculator converts it by reference to the absorbance curve mentioned into corresponding values for the instantaneous volume-related or specific blood content B(t). An electrical signal corresponding to the blood content thus becomes available from the output of converter 14.

The instantaneous blood loss V(t) can be found by multiplying the signal B(t) by a signal Q(t) representing the volume of flow, the latter being generated in a known fashion by the flow meter 5. Thus, for the purpose of forming a product, the two electrical signals B(t) are Q(t) are fed to the inputs of a multiplier whose output signal gives an absolute indication of any blood loss there may be. It will be appreciated that this presupposes that all the signal emitting and signal converting components have previously been calibrated and harmonised.

The signal V(t) may be fed to a visual indicator instrument 16 to allow the instantaneous blood loss to be monitored continuously. In addition, this signal may be fed to the input of a first alarm 17 which is set to a specific value for the instantaneous blood loss and gives a visual and/or acoustic signal when this value is exceeded is indicated by the symbols on the drawing. To the operator this signal will mean that the instantaneous blood loss is too high and must be stopped by coagulating the injured vessel.

Finally, the signal V(t) which expresses the instantaneous blood loss may be continuously integrated by means of an integrator 18 and displayed by an indicator instrument 19, so that after, and especially during, an operation the blood loss V can be read off so that a decision can be taken as to whether in the circumstances a blood transfusion has to be given to make good the loss of blood. In addition, the signal representing the blood loss V may also be fed to the input of a second alarm 20, which also gives a visual and/or acoustic warning signal, when an adjustable threshhold value for blood loss is exceeded, this signal usefully being distinguished from the signal from the first alarm 7. e.g. by arranging the light signal to be of different intensity or colour, and/or by the acoustic signal being of different intensity or pitch.

In the embodiment described, what is used to determine the specific blood content B(t) is the colour density of the outgoing irrigating water, which is one of its characteristics which changes with blood content. Since the electrical conductivity for example of the irrigating water also alters with the blood content, the procedure could be to measure the resistance of the ingoing and outgoing irrigating water and to generate a difference signal a(t) on this basis. Capacitive measurements could also be made by allowing the ingoing water to act on the dielectric of a first measuring capacitor and the outgoing water on the dielectric of a second measuring capacitor, whose capacity thus alters relative to that of the first capacitor as a function of blood content, with the result that a signal a(t) representing the blood content can be generated by making a continuous comparison between the capacities, from which signal the instantaneous blood content B(t) can in turn be calculated from a standard reference curve (not shown).

We claim:

1. In a method for determining blood losses during endoscopic operations, in a body cavity and in particular during transurethral resectomy, of the kind in which continuous irrigation is employed, using sterilised, flushing water which is fed into the body cavity through the endoscope and fed out again mixed with the blood which has been lost, the invention which, comprises the steps of measuring the rate of flow Q(t) of the outgoing flushing water, determining the specific blood content B(t) from one of the characteristics of the outgoing water which varies with the blood content and, to determine the blood loss V(t), comparing said specific blood content with the rate of flow Q(t) of the outgoing flushing water.

2. A method according to claim 1, wherein the colour density (absorbance) of the outgoing irrigating water is compared with the colour density of the ingoing irrigating water and the instantaneous blood content B(t) is determined from the value a(t) given by comparison to a reference absorbance curve for blood in water.

3. Apparatus for carrying out the method according to claim 1, comprising an endoscope equipped with means for supplying ingoing flushing water to the body cavity, means to monitor the determination of blood loss, means to determine the specific blood content B(t), means for supporting the outgoing water from the body cavity to determine the specific blood content B(t), a flow meter to measure the rate of flow Q(t) of the outgoing flushing water, and means for comparing said specific blood content with said rate of flow to determine instantaneous blood loss V(t) and/for delivering an electrical signal corresponding to the blood loss to said monitor means.

4. Apparatus according to claim 3 comprising means for comprising the colour density (absorbance) of the outgoing irrigating water with the colour density of the ingoing irrigating water, means for determining said instantaneous blood content B(t) from the value a(t) given by said comparison by reference to an absorbance curve for blood in water.

5. Apparatus according to claim 3, which comprises further a chamber through which the ingoing irrigating water flows and a chamber through which the outgoing irrigating water flows, means for irradiating said chambers with light from one side, each said chamber having associated with it, on the side remote from said irradiating means, a photoelectric receiver on which the light emerging from the associated chamber impinges, and means for generating an electrical output signal from said receivers, a difference amplifier to which said two output signals are fed and therein subtracted, to form a difference signal a(t) a measured value converter for converting said difference signal a(t) into a signal representing said specific blood content B(t) by reference to the absorbance curve for blood in water, and, in order to determine blood loss V(t), means are provided for multiplying said latter signal by a signal representing the rate of flow Q(t) of the outgoing irrigating water.

6. Apparatus according to claim 3, and further comprising first alarm means to which the electrical signal representing said instantaneous blood loss V(t) is passed said first alarm means being arranged to sound an alarm signal when a given adjustable threshold value is exceeded.

7. Apparatus according to claim 6, and further comprising an integrator in which the signal representing the instantaneous blood loss V(t) is integrated, said integrator being arranged to deliver an output signal, which represents the total blood loss V, means for feeding said output signal to the input of a second alarm means arranged to give an alarm signal when a given adjustable threshold value is exceeded, the second alarm signal differing from the first signal from said first alarm means.

8. Apparatus according to claim 3, and further comprising means for visually displaying the values for instantaneous blood loss V(t) and for total blood loss V.

* * * * *